United States Patent [19]

Greco et al.

[11] Patent Number: 5,252,247
[45] Date of Patent: Oct. 12, 1993

[54] METAL (DIALKYLAMINOALCOHOLATE) SOLUTIONS

[75] Inventors: Carl C. Greco, Garnerville; Johst H. Burk, Mohegan Lake, both of N.Y.

[73] Assignee: Akzo America Inc., Dobbs Ferry, N.Y.

[21] Appl. No.: 668,533

[22] Filed: Mar. 13, 1991

Related U.S. Application Data

[63] Continuation of Ser. No. 270,570, Nov. 14, 1988, abandoned.

[51] Int. Cl.$^5$ ................................................ C09K 3/00
[52] U.S. Cl. ................................ 252/182.12; 534/15; 556/76
[58] Field of Search ................ 252/182.12; 534/15; 556/76

[56] References Cited

U.S. PATENT DOCUMENTS

| | | | |
|---|---|---|---|
| 1,990,442 | 2/1935 | Traube et al. | 556/76 |
| 2,446,682 | 8/1946 | Whitner | 556/113 |
| 3,094,546 | 6/1963 | Towers | 534/15 |
| 3,278,571 | 10/1966 | Mazdiyasni et al. | 534/15 |
| 3,356,703 | 12/1967 | Mazdiyasni et al. | 534/15 |
| 3,479,381 | 11/1969 | Mitchell | 534/15 |
| 3,757,412 | 9/1973 | Mazdiyasni et al. | 534/15 |
| 3,932,545 | 1/1976 | Screttas | 502/155 |
| 4,264,370 | 4/1981 | Turner | 106/264 |
| 4,287,131 | 9/1981 | Langer | 556/174 |
| 4,489,000 | 12/1984 | Gradeff et al. | 534/15 |
| 4,507,245 | 3/1985 | Ozaki et al. | 534/25 |
| 4,670,573 | 6/1987 | Greco et al. | 556/182 |
| 4,764,357 | 8/1988 | Sherif et al. | 423/338 |
| 4,801,692 | 1/1989 | Gradeff et al. | 534/15 |
| 4,837,190 | 6/1989 | Summers et al. | 534/15 |
| 4,839,339 | 6/1989 | Bunker et al. | 505/1 |
| 4,847,239 | 7/1989 | Piotrowski et al. | 505/801 |
| 4,900,536 | 2/1990 | Snyder et al. | 423/593 |
| 4,920,093 | 4/1990 | Nonaka et al. | 505/1 |
| 5,021,395 | 6/1991 | Druliner et al. | 505/1 |
| 5,024,991 | 6/1991 | Tsunashima et al. | 505/1 |
| 5,028,667 | 7/1991 | McLain et al. | 525/415 |
| 5,099,006 | 3/1992 | Gradeff et al. | 534/15 |
| 5,106,828 | 4/1992 | Bhargava et al. | 505/1 |

FOREIGN PATENT DOCUMENTS

| | | |
|---|---|---|
| 62-240691 | 10/1987 | Japan . |
| 84/01045 | 1/1985 | PCT Int'l Appl. . |
| 712828 | 8/1954 | United Kingdom ................ 556/76 |
| 1188974 | 4/1970 | United Kingdom . |

OTHER PUBLICATIONS

Wheeler et al., *J. Am. Pharm. Assoc.*, Sci. Ed., XXXIII, No. 5, 156–158 (May 1949) "Dihydroxypropyl Bismuthale".

Ojima et al, *Zeitschrift fur Anorganische und Allgemeine Chemie*, 309 (1961), pp. 110–120.

Hein et al., *Z. fur Anorganische Allgemeine Chemie*, 282 (1955), pp. 93–209.

Smolander, *Inorg. Chim. Acta.*, 128 (1), pp. 61–63 (1987).

*Primary Examiner*—Edward A. Miller
*Attorney, Agent, or Firm*—Richard P. Fennelly; Louis A. Morris

[57] ABSTRACT

Solubilized metal (dialkylaminoalcoholate) compounds in organic solvent can serve as a source of metal values for metal oxide-containing superconductor compositions. Stable solutions, resistant to precipitation problems, can be formed by reaction of a dialkylaminoalkanol with a metal alkoxide followed by removal of by-product alkanol by vacuum distillation below the reflux temperature of the solution. Exemplary metals include copper, yttrium, barium, calcium, and bismuth, lanthanum and strontium.

4 Claims, No Drawings

METAL (DIALKYLAMINOALCOHOLATE) SOLUTIONS

This is a continuation of application Ser. No. 270,570 filed Nov. 14, 1988, now abandoned.

BACKGROUND OF THE PRESENT INVENTION

1. Field of the Invention

The present invention relates to metal (dialkylaminoalcoholate) solutions which can serve, for example, as a source of metal for the manufacture of metal oxide superconductor compositions.

2. Description of the Prior Art

There is currently much interest in high $T_c$ superconductor compositions which are metal oxides. Representative metal components in such compositions include: copper, yttrium, barium, calcium, bismuth, lanthanum, strontium, and the like. These metal moieties are termed "metal oxide superconductor precursor" metals in accordance with the present invention which is directed to certain novel compounds containing such precursor moieties, solutions containing them which find use in conjunction with chemical means to form the ultimately desired superconductor metal oxide composition, and to certain processes for forming the compounds and solutions.

The prior art description of the copper complexes of dialkylaminoalcoholate solutions, for example, appears to focus on aqueous solutions. For example, U.S. Pat. No. 2,446,682 mentions their use to modify cellulose textiles and names diethylethanolamine (Col. 7, line 38) and methyldiethanolamine (Col. 7, line 41) as representative alkylolamines which can be used. Ojima et al. in Z. fur Anorganische und Allgemeine Chemie, Band 309 (1961) pp. 110–120 mentions (on pages 110–111) that the state of knowledge about the structure and properties of copper complexes of ethanolamine and its derivatives formed in aqueous solution seemed to be "limited" at the time of their work. Ojima et al. cited earlier work by Hein et al. (Z. Anorg. Allg. Chem., 282, 93 (1955) in regard to their review of the prior art. Hein et al. only show halide-containing complexes. There is no showing or suggestion of organic solvent/alkoxide compositions or their use in making metal oxide superconductor compositions.

The prior art description of calcium alkoxides also appears to be devoid of the novel calcium (dialkylaminoalcoholates) of the instant invention. U.S. Pat. No. 4,287,131 indicates, at Col. 1, lines 52–55, that certain metal alkoxide derivatives of $C_1$–$C_{10}$ alkanolamines can be formed without a clear suggestion that a dialkyl moiety "Z" is to be chosen. No exemplification of any calcium (dialkylaminoalcoholate) appears in this patent. International Patent Publication No. WO 85/00365 mentions the possibility of contacting CaO or CaOH with an "activator" and names N-methylethanolamine, a monoalkyl-substituted amine compound, on page 31 thereof (last one). Finally, British Patent No. 1,188,974 indicates (page 3, lines 40 et seq.) formation of metal alcoholates from amino alcohols. It exemplifies a calcium (dialkoxyalkylaminoalcoholate in Example 34 and a calcium (dialkylaminoalcoholate) having oxygen atom interruption in its alkylene moiety in Example 52.

SUMMARY OF THE PRESENT INVENTION

The present invention relates to organic solutions containing a soluble metal alkoxide (i.e., a metal (dialkylaminoalcoholate)) which can serve as a stable and convenient source of metal, e.g., for use in making metal oxide-containing superconductor compositions. The metal (dialkylaminoalcoholate) compositions of the present invention are essentially halide-free. The instant invention also relates to certain novel metal (dialkylaminoalcoholate) compounds and to certain novel processes for forming the solutions.

DETAILED DESCRIPTION OF THE PRESENT INVENTION

It is highly desirable to be able to produce organic solutions containing solubilized metal alkoxides. Such solutions can serve as a source of the metal for a metal oxide superconductor composition. The presence of the solubilized metal alkoxide makes it much easier for the person of ordinary skill in the art to measure more accurately the available metal values for combination with other solubilized metal alkoxides in making metal oxide superconductors. However, it has been difficult heretofore to obtain soluble solutions of the desired metal alkoxides which possessed good storage stability. They would have a tendency to precipitate metal values from solution, thereby rendering it difficult to give an accurate measure of the available (solubilized) metal values still in solution.

The present invention relates to solubilized metal dialkylaminoalcoholate compounds which have good storage stability. These compounds are of the formula $M(ORNR'_2)_2$ where M is a superconductor metal precursor, R is alkylene of from 2 to 3 carbon atoms and R' is alkyl of from 1 to 8 carbon atoms, with the proviso that if R' is straight chain, the number of carbon atoms in the straight chain is no more than 3. Preferred ligand systems are those which can form 5- or 6-membered rings with the central metal atom via internal coordination between the nitrogen atom on the ligand and the metal atom. Examples of suitable metal precursors for the metal oxide superconductor include copper, yttrium, barium, calcium, bismuth, lanthanum, strontium and the like.

Depending upon the reactivity between the metal moiety desired and the dialkylaminoalcohol of choice, the reaction for forming the desired compounds can be conducted from either the metal per se or a metal alkoxide. It has been found that the metal per se can be used in cases where the superconductor metal precursor is calcium, barium or strontium, preferably by ball milling the metal to activate it as described in U.S. Pat. No. 4,670,573. When the metal moiety is the more non-reactive copper, bismuth or yttrium, for example, an appropriate conventional metal alkoxide thereof is the desired starting material for reaction with the selected dialkylaminoalcohol.

The compounds described above can be easily formed by a two-step procedure when the metal alkoxide is the desired reagent. The first stage can involve the formation of a metal alkoxide by reaction of a metal salt (e.g., a copper halide such as cupric chloride) with an alkali metal alcoholate (such as lithium methoxide). The alkali metal alcoholate is formed by reaction between an alcohol and molten alkali metal. This reaction is conducted in a, solvent medium, most preferably the alcohol chosen for reaction with the alkali metal. The metal alkoxide that is formed can be freed of impurities by washing with the alcohol.

Once the metal alkoxide has been formed it can be suspended in a solvent (such as toluene, trimethylbenzene, or the like) and reacted with a dialkylaminoalkanol. This reaction forms the desired metal (dialkylaminoalcoholate) compounds and alcohol by-product. The alcohol by-product, if removed by vacuum distillation at temperatures below the reflux temperature (e.g., about 35°–50° C.), will enable the production of a solution of the dialkylaminoalcoholate which has good resistance to precipitation problems.

The present invention is further understood by reference to the Examples which follow.

EXAMPLE 1

In 600 cc of methanol was dissolved 34 grams of copper(II) chloride (0.253 mole). To this solution was added 5 grams of lithium (0.725 mole). The solution was stirred for four hours at room temperature. At the end of this time there was formation of a blue solid precipitate (copper methoxide). The precipitate was filtered from the reaction mixture and was washed four times. with 250 cc of methanol each time to remove LiCl and unreacted copper chloride. The blue solid was vacuum dried in the vacuum oven at 40° C. under nitrogen, and was then suspended in 400 cc of toluene. To this slurry was added 86 grams (0.76 mole) of diethylaminoethanol over a 10 minute period. The reaction mixture was heated to 35° C. under a vacuum of 25 mm of mercury for 45 minutes to remove the methanol. About 100 cc of methanol-toluene was distilled off during this time, keeping the pot temperature below 40° C. A clear dark blue solution resulted after the heating period and was diluted with more toluene to arrive at a final weight of 668 grams. The amount of copper alkoxide, of the formula $Cu(OCH_2CH_2N(Et)_2)_2$, in this solution was 74.8 grams or 11.2% by weight.

The material was stored in a dry box for several weeks with no evidence of any precipitation. A portion of this material was mixed with a solution of barium diethylaminoethoxide and allowed to stand at room temperature under nitrogen. This solution was also stable for many weeks. No sign of precipitation was noted.

EXAMPLE 2

The same procedure described in Example 1 was used with the exception that dimethylaminoethanol was used as the alcoholic ligand in the preparation of the copper/barium alkoxide mixture wherein the copper compound had the formula $Cu(OCH_2CH_2N(Me)_2)_2$. Similarly, no precipitation was observed for the resulting solution after several weeks.

EXAMPLE 3

To a one liter flask was added 100 grams of the copper alkoxide solution from Example 1 (the solution was analyzed for copper and found to contain 2.52% Cu). While under a nitrogen atmosphere, there was added 77 grams of a barium diethylaminoethylate solution. This solution was analyzed and found to contain 4.7% barium. The above solution was then mixed with 26 grams of a yttrium diethylaminoethylate solution containing 4.6% yttrium. The resulting solutions were stirred at room temperature for one hour and then allowed to stand at room temperature for an infinite period of time. After two months standing, no sign of precipitation was noted.

COMPARATIVE EXAMPLE 4

To 800 cc of methanol was added 40 grams of copper(II) chloride (0.297 mole) which produced a green colored solution. To this solution was then added 38.4 grams of butyl lithium (0.6 mole) in hexane over a 30 minute period. The temperature rose to 50° C. and a blue precipitate formed. The reaction mixture was stirred for six hours at room temperature. The reaction mixture was filtered and the precipitate (copper methoxide) was suspended in toluene and was distilled to dryness at 80° C./60 mm of Hg. The solid that remained was redissolved in toluene and was reacted with more butyl lithium to insure all of the copper chloride had reacted. The reaction mixture was filtered again, and the precipitate was washed three times with 150 cc of methanol. The precipitate was vacuum dried and was again suspended in toluene (500 cc). To this slurry was then added 59 grams of dimethylaminoethanol (0.6 mole plus 10% excess). The reaction was heated to reflux (about 64° C.) and the methanol azeotroped with the toluene. It took two hours to remove all traces of methanol from the solution. The solution that remained was a dark navy blue color and was filtered at room temperature. The filtrate was allowed to stand at room temperature under nitrogen. The next day a great deal of solids had come out of solution. After a week, more solids came out of solution.

EXAMPLE 5

This Example illustrates the preparation of a mixed solution of yttrium, barium and copper diethylaminoethoxide.

A solution of 60 grams of yttrium diethylaminoethoxide in toluene (4.6% Y) was mixed with a solution of barium diethylaminoethoxide (23 grams) in mesitylene. The mesitylene-barium solution weighed 181 grams. The resulting solution weighed 241 grams. This clear-yellow solution was stripped to a weight of 51.6 grams [23 grams of $Ba(OCH_2CH_2NEt_2)_2$ and 13.5 grams of $Y(OCH_2CH_2NEt_2)_3$ in solution].

To the above solution was then added 227 grams of a copper diethylaminoethoxide-mesitylene solution containing 2.6% copper. The resulting dark blue solution was stirred at 40°–50° C for one hour. The solution by analysis contained 0.031 mole of the yttrium alkoxide, 0.062 mole of the barium alkoxide and 0.093 mole of the copper alkoxide. This solution was storage stable for over two months with no sign of precipitation. The solution comprised around a 22% concentration of the metal alkoxides.

EXAMPLE 6

This Example illustrates preparation of barium diethylaminoethoxide solution.

In a 1-L, 3-neck flask was added 22 grams of barium metal (0.16 mole) into 400 cc of trimethylbenzene or mesitylene. To this solution was added 56 grams of diethylaminoethanol (0.48 mole) over a 10 minute period. The reaction mixture was heated to reflux where hydrogen started to evolve. The reaction mixture was refluxed for three hours during which hydrogen was continually coming from the reaction. Then the mixture was cooled and filtered. The filtrate, a yellow-orange solution, weighed 458 grams. This filtrate was analyzed and found to contain 4.7% barium which corresponds to 57.9 grams of the desired alkoxide (98% yield).

EXAMPLE 7

This Example illustrates the preparation of a calcium diethylaminoethoxide solution.

Same procedure as above in Example 6 except that 14.5 grams of calcium (0.36 mole), which had been premilled with a catalytic amount (about 0.1 gm/25 gm of calcium) of mercury chloride, was used in 500 cc of toluene. To this was added 126 grams of diethylaminoethanol (1.1 moles). Hydrogen was given off during a 24 hour reflux period. The filtrate weighed 624 grams. Analysis showed that the filtrate contained 1.5% calcium (9.36 grams). The yield was 65% of the desired calcium diethylaminoethylate based on the calcium analysis.

EXAMPLE 8

This illustrates preparation of a bismuth diethylaminoethoxide solution.

In a 1-L, 3-neck flask was added 20 grams of bismuth methoxide (0.066 mole). To this, under $N_2$, was then added 400 cc of mesitylene and 100 cc of toluene. The reaction was equipped with a Dean-Stark apparatus. Dimethylaminoethanol (17.8 grams, 0.2 mole) was added, and the reaction was heated to reflux. During the reflux period 120 cc of a toluene-methanol mixture was azeotroped off over a two hour period. Most of the bismuth methoxide had gone into solution and reacted. The reaction mixture was filtered using a CELITE filter cake as the filtering aid. The filtrate weighed 414 grams and was analyzed to contain 2.5% Bi. According to the analysis the amount of bismuth diethylaminoethylate formed was 23.4 grams (75% yield).

EXAMPLE 9

In a one liter, three neck flask was suspended 25 grams of lanthanum metal (0.18 mole) and 0.5 grams of mercury sulfate into 400 cc of toluene. To this slurry was added 96 grams of diethylaminoethanol (0.82 mole). The resulting reaction mixture was heated to reflux with vigorous evolution of hydrogen. The reaction was filtered after refluxing for twelve hours. The filtrate was distilled to constant weight until an orange-yellow semisolid remained. It weighed 6.4 gram which represented an 88% yield of the desired lanthanum diethylaminoethylate. This alkoxide product was redissolved in toluene to form a stable solution at around 20% concentration.

The organic solvent solutions containing the subject metal (dialkylaminoalcoholate) compounds can be used to make metal oxide superconductor compositions as described before. The first step is to make a series of solutions (or a mixed solution) of the desired superconductor metal moieties (e.g., a series of solutions, or a mixed solution of yttrium, barium and copper dialkylaminoalcoholate compounds). If a mixed solution is made, the metal moieties are present in the molar ratios desired in the final superconductor composition. If separate solutions containing each respective metal moiety are made, they would be combined in the appropriate ratios to yield the metal moieties in such ratios. Next, the organic solvent solutions containing these metal (dialkylaminoalcoholate) compounds are hydrolyzed to form a gel by being mixed with a mixture of water and an alcohol which is miscible with the organic solvent (e.g., ethanol, isopropanol or an alkoxy alcohol such as methoxypropanol). The gel can be isolated by evaporation of the solvent and then can be fired to dry and fuse it into the desired superconductor composition.

The foregoing Examples illustrate certain embodiments of the instant invention but should not be construed in a limiting sense as defining the scope of protection desired. The claims which follow set forth the scope of protection desired.

We claim:

1. A solution which consists essentially of: (a) an organic solvent; and (b) a metal (dialkylaminoalcoholate) compound dissolved therein, the metal being a metal oxide superconductor precursor selected from the group consisting of yttrium, bismuth, and lanthanum.

2. A solution as claimed in claim 1 wherein the metal is yttrium.

3. A solution as claimed in claim 1 wherein the metal is bismuth.

4. A solution as claimed in claim 1 wherein the metal is lanthanum.

* * * * *